(12) United States Patent
Dolan et al.

(10) Patent No.: US 8,303,639 B2
(45) Date of Patent: Nov. 6, 2012

(54) RELEASABLE POLYMER ON DRUG ELUTION STENT AND METHOD

(75) Inventors: Mark Dolan, Santa Rosa, CA (US); Matthew J. Birdsall, Santa Rosa, CA (US); Eugene Tedeschi, Santa Rosa, CA (US); Joseph Berglund, Santa Rosa, CA (US); Raffy Brown, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1139 days.

(21) Appl. No.: 11/689,733

(22) Filed: Mar. 22, 2007

(65) Prior Publication Data

US 2008/0234808 A1 Sep. 25, 2008

(51) Int. Cl.
*A61F 2/06* (2006.01)
(52) U.S. Cl. ............ 623/1.11; 623/1.42; 623/1.46
(58) Field of Classification Search ............ 623/1.15, 623/1.42–1.48
See application file for complete search history.

(56) References Cited

U.S. PATENT DOCUMENTS

| | | | |
|---|---|---|---|
| 5,304,121 A | 4/1994 | Sahatjian | |
| 5,323,778 A * | 6/1994 | Kandarpa et al. | 600/411 |
| 5,665,077 A * | 9/1997 | Rosen et al. | 604/266 |
| 6,409,716 B1 | 6/2002 | Sahatjian et al. | |
| 2002/0128704 A1 | 9/2002 | Daum et al. | |
| 2003/0083646 A1* | 5/2003 | Sirhan et al. | 604/891.1 |
| 2004/0127886 A1 | 7/2004 | Daum | |
| 2005/0043718 A1* | 2/2005 | Madhani et al. | 606/1 |
| 2005/0278014 A9 | 12/2005 | Daum et al. | |
| 2005/0287184 A1* | 12/2005 | Hossainy et al. | 424/423 |

* cited by examiner

*Primary Examiner* — Tuan V Nguyen
*Assistant Examiner* — Thomas McEvoy

(57) ABSTRACT

A method for treating a vascular condition is disclosed, the method comprising delivering a stent to a target region of a vessel, the stent including a drug polymer coating including an elution portion and a remaining portion, eluting the elution portion from the delivered stent for an elution period, heating the delivered stent after the elution period; and removing the remaining portion based on the heating.

20 Claims, 7 Drawing Sheets

10

10

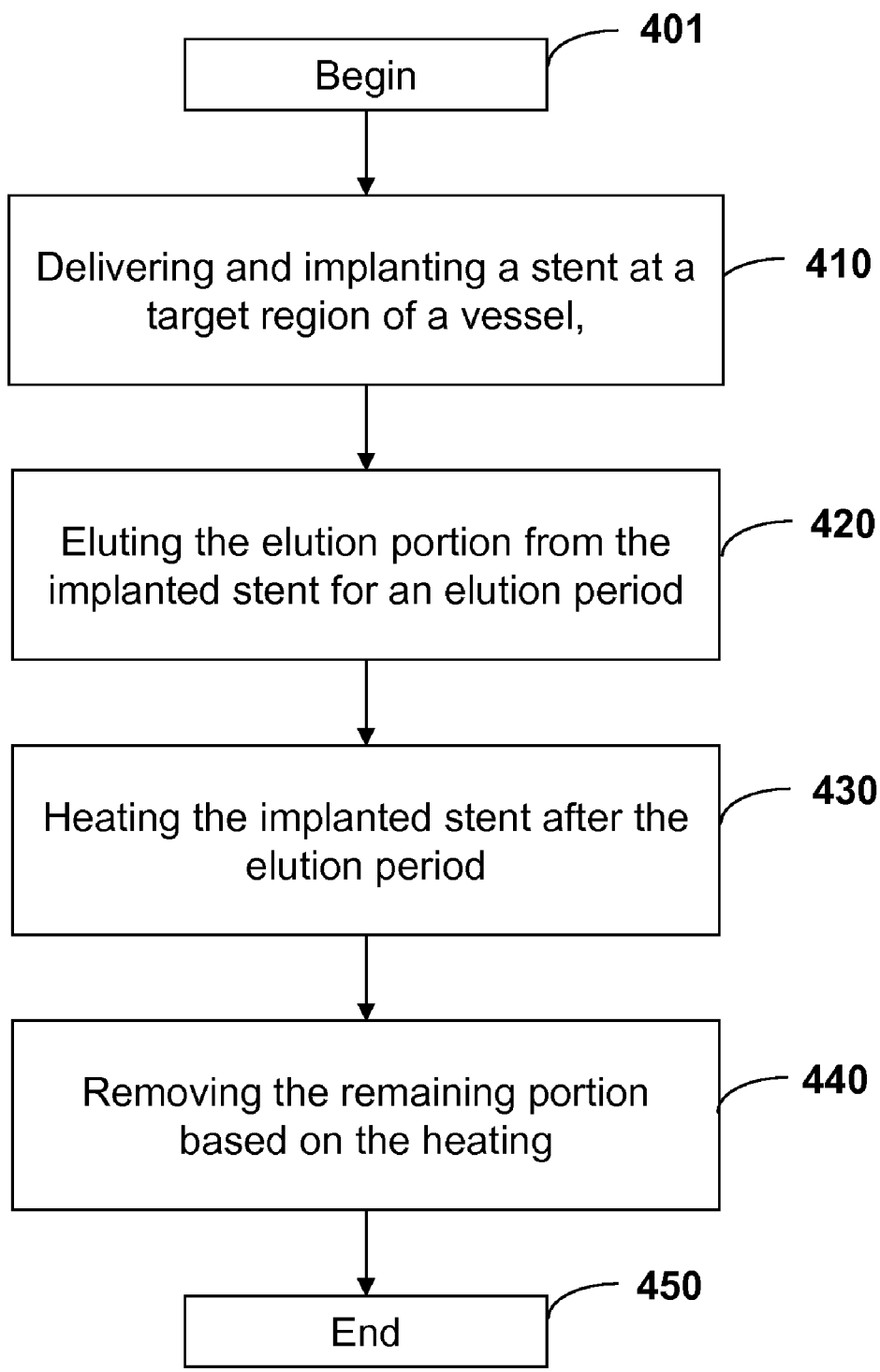

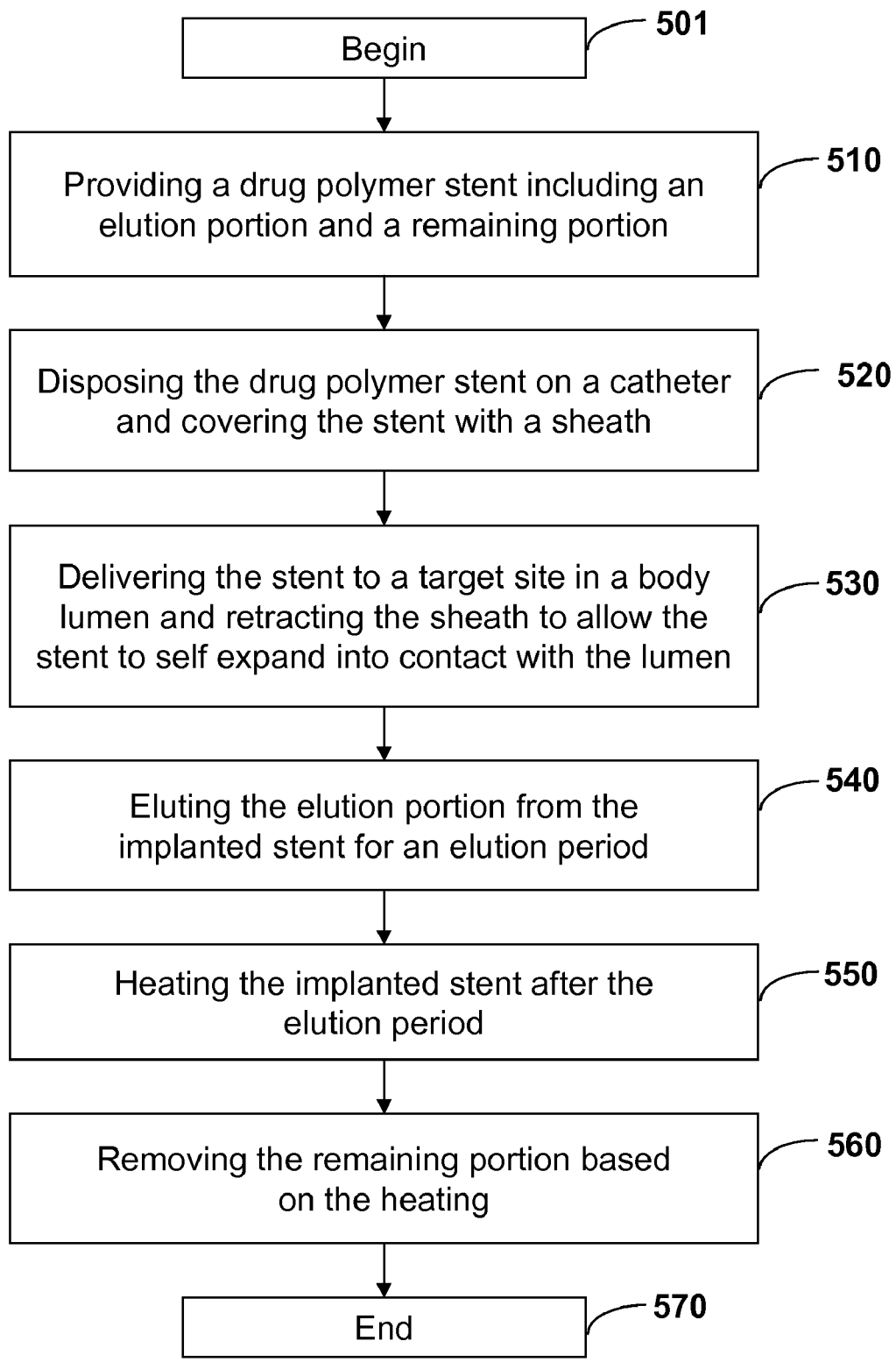

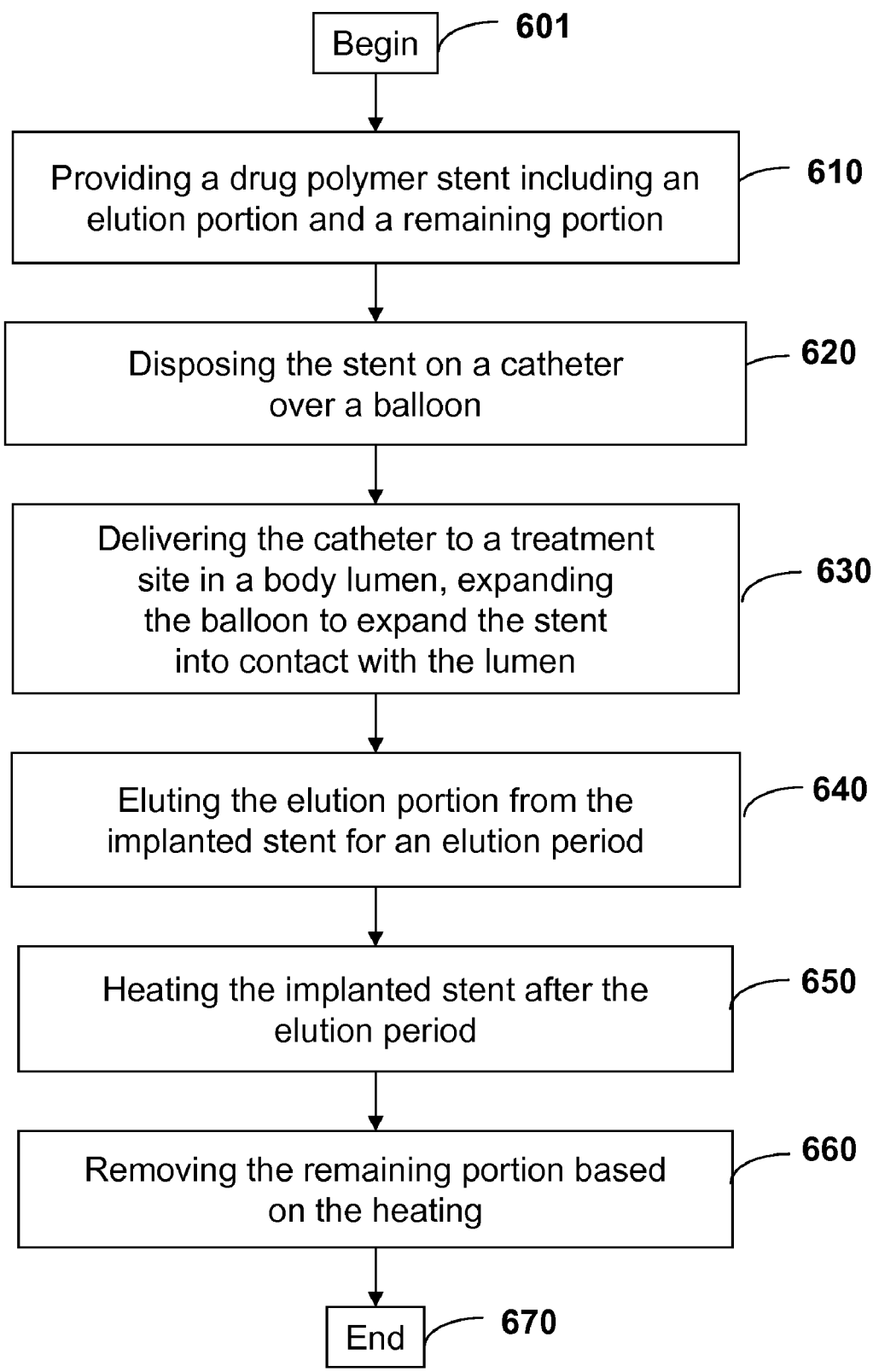

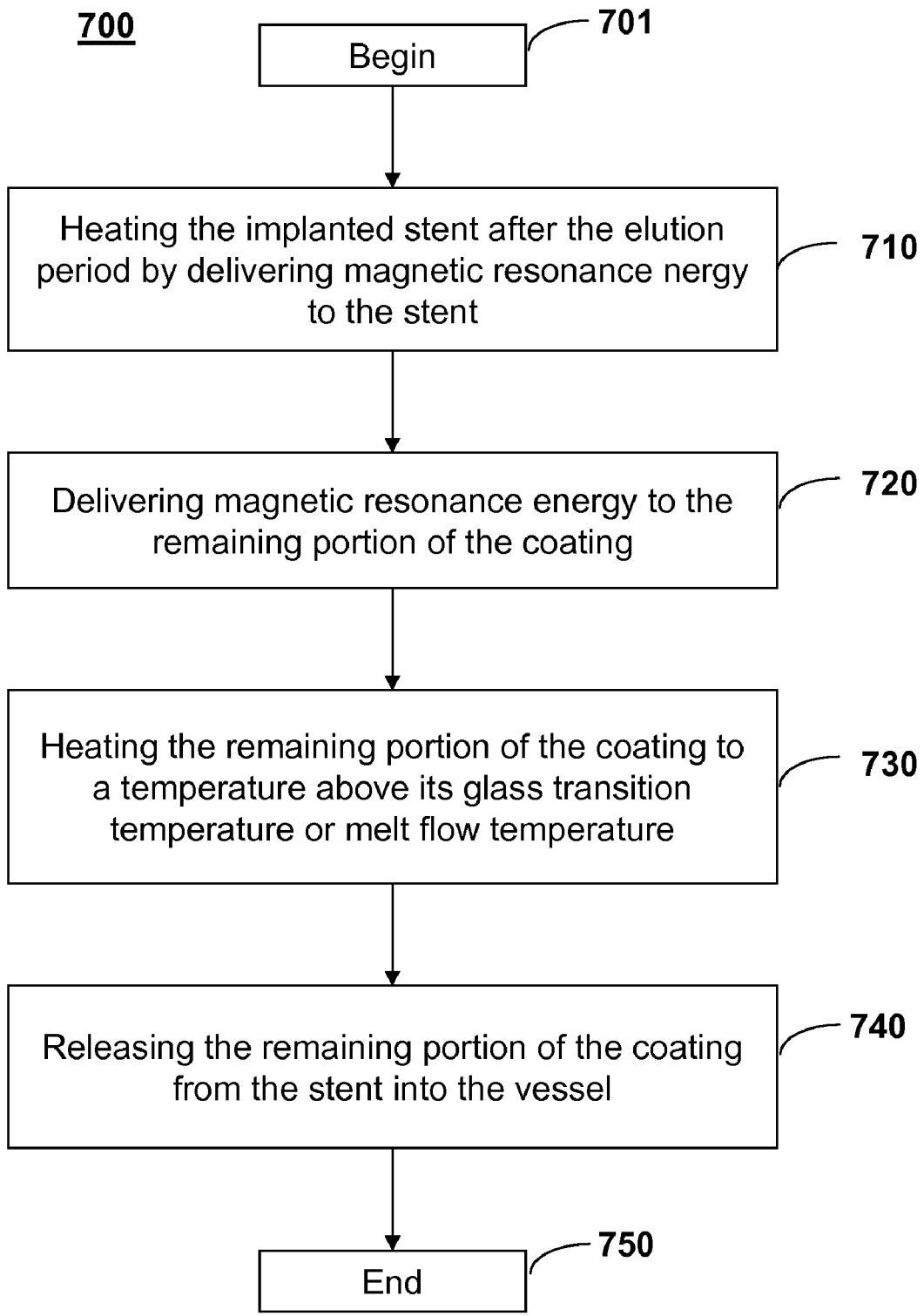

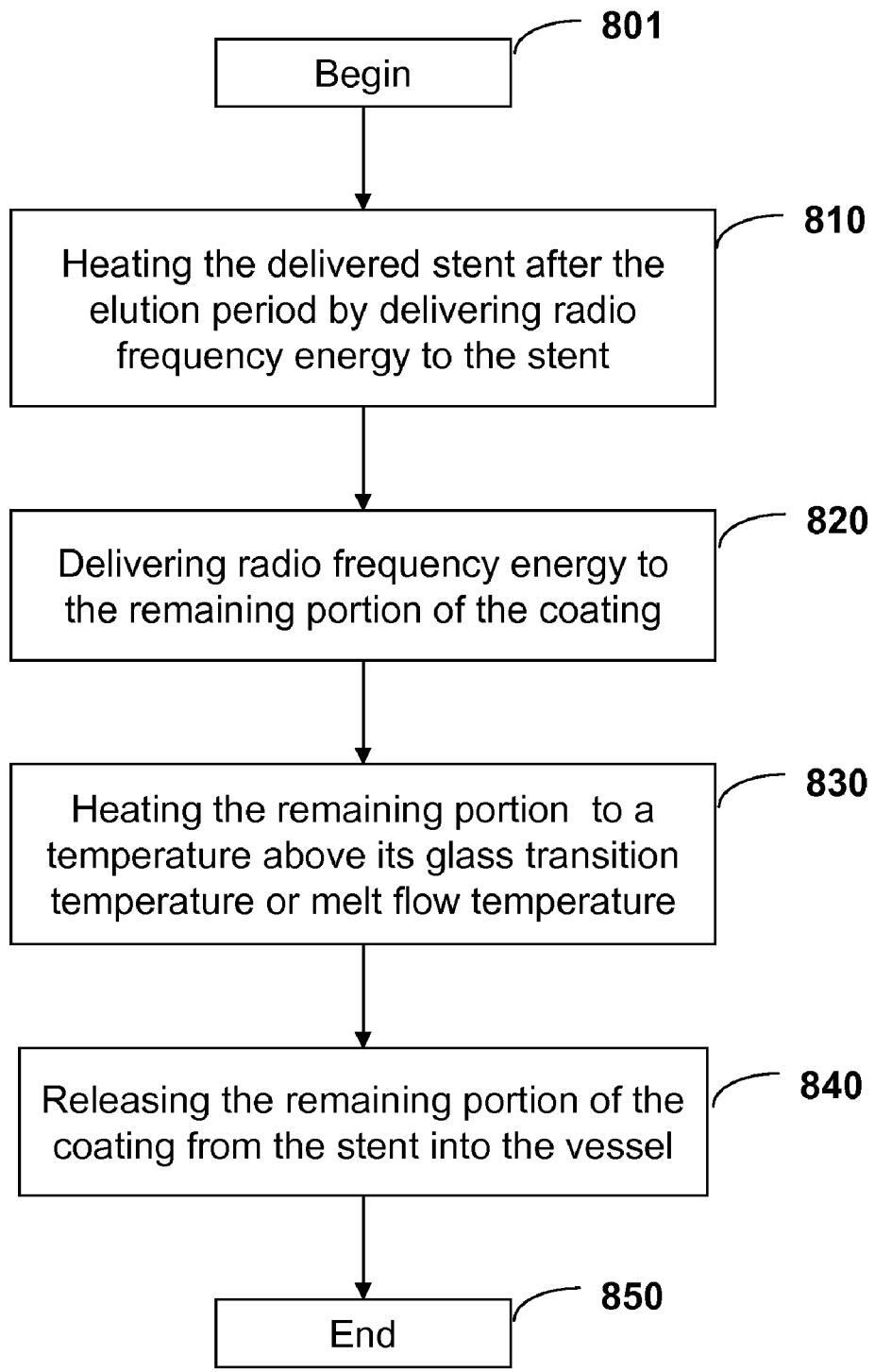

RELEASABLE POLYMER ON DRUG ELUTION STENT AND METHOD

TECHNICAL FIELD

This invention relates generally to biomedical stents. More particularly, the invention relates to an endovascular stent with a polymer coating carrying a drug for in vivo, timed-release, and a method for removing the remnants of the polymeric coating after drug delivery.

BACKGROUND OF THE INVENTION

Drug-coating stents can improve the effectiveness of stents by effective therapeutic compounds or drugs to the target site. For example, anti-inflammatory or anti-thrombogenic compounds may be carried by a drug-polymer coating and released after insertion and deployment of the stent. These drugs and coatings can reduce the trauma to the local tissue bed, aid in the healing process, and significantly reduce the narrowing or constriction of the blood vessel that can recur after stent placement.

The ideal drug polymer coating must be able to adhere strongly to the metal stent framework both before and after delivery of the stent, and be able to control release the drug at sufficient therapeutic levels for several days, weeks or longer. Unfortunately, some drug polymers remain on the stent after their function of drug delivery has been completed. Polymer remaining on the stent after drug elution may cause an unfavorable result, such as thrombogenesis.

It would be desirable, therefore, to have a method for removing the polymer coating from a polymer coated drug delivery stent after drug elution that overcomes these and other disadvantages.

SUMMARY OF THE INVENTION

One aspect of the invention provides a method for treating a vascular condition. The method includes delivering a stent to a target region of a vessel, the stent including a drug polymer coating. The drug polymer coating includes an elution portion and a remaining portion. The method continues by eluting the elution portion from the delivered stent for an elution period, heating the delivered stent after the elution period and removing the remaining portion based on the heating.

Another aspect of the invention provides a method for treating a vessel in a body. The method includes providing a stent including a biodegradable polymeric coating carrying at least one therapeutic agent, the coating being selected from the group consisting of bioproteins, sugar and dextran, the coating having a first delivery configuration and a second, post-delivery configuration including a remaining portion of the polymeric coating. The method further includes delivering the stent to a targeted region of the vessel, allowing the stent to remain in the targeted region in a first configuration for a predetermined length of time for elution of the at least one therapeutic agent and removing the remaining portion of the polymeric coating from the stent by heating the stent in situ in the vessel, the polymer coating being substantially removed from the stent based on the heating.

Yet another aspect of the invention provides a method for treating a vessel in a body. The method includes the steps of providing a polymer coated drug delivery stent including a polymer coating carrying at least one therapeutic agent, delivering the stent to a targeted region of the vessel and allowing the delivered stent to remain in the targeted region for a predetermined period of time during which the polymeric coating elutes at least one therapeutic agent to the targeted region of the vessel. After elution of the therapeutic agent, the method continues to include heating the stent and releasing a remaining portion of the polymer coating into the vessel while leaving the stent in the targeted region of the vessel, and substantially removing the polymer coating from the stent based on the heating.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

BRIEF DESCRIPTION OF THE DRAWINGS

FIG. 4 is a flow diagram of a method for treating a vascular structure in accordance with one embodiment of the current invention;

FIG. 5 is a flow diagram of a vascular treatment method in accordance with one embodiment of the current invention; and FIG. 6 is a flow diagram of a vascular treatment method in accordance with another embodiment of the current invention.

FIG. 7 is a flow diagram of a method of manufacture in accordance with another aspect of the current invention; and FIG. 8 is a flow diagram of a method of manufacture in accordance with another aspect of the current invention.

DETAILED DESCRIPTION

The invention will now be described by reference to the drawings wherein like numbers refer to like structures.

Figure 1:
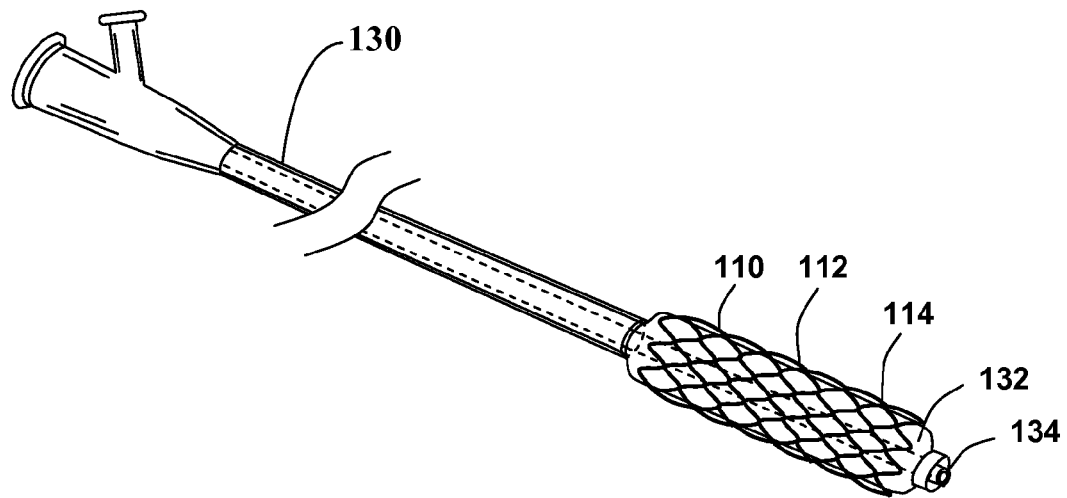
FIG. 1 is a schematic representation of a stent delivery system.

FIG. 1 shows an illustration of a system for treating a vascular condition, comprising a drug polymer stent 110 coupled to a catheter 130 in accordance with one embodiment of the present invention at 100. Drug polymer stent with catheter 100 includes a drug polymer stent 110 coupled to a delivery catheter 130. Drug polymer stent 110 includes a generally tubular stent framework 112 and a drug polymer portion 114 (shown in detail in FIG. 2).

Catheter 130 of an exemplary embodiment of the present invention includes a balloon 132 that expands and deploys the drug polymer stent within a vessel of the body. After positioning drug polymer stent 110 within the vessel with the assistance of a guide wire traversing through a guide wire lumen 134 inside catheter 130, balloon 132 is inflated by pressurizing a fluid such as a contrast fluid or saline solution that fills a tube inside catheter 130 and balloon 132. Drug polymer stent 110 is expanded until a desired diameter is reached, and then the contrast fluid is depressurized or pumped out, separating balloon 132 from stent 110 and leaving stent 110 deployed in the vessel of the body. Alternately, catheter 130 may include a sheath that retracts to allow expansion of a self-expanding version of stent 110. The stent is inserted typically in a controlled environment such as a catheter lab or hospital. A delivery catheter, which helps position the stent in a vessel of the body, is typically inserted through a small incision of the leg and into the femoral artery, and directed through the vascular system to a desired place in the vessel. Guide wires threaded through an inner lumen of the delivery catheter assist in positioning and orienting the stent framework. The position of the stent may be monitored, for example, with a fluoroscopic imaging system or an x-ray viewing system in conjunction with radiopaque markers on the stent, radiopaque markers on the delivery catheter, or contrast fluid injected into an inner lumen of the delivery catheter and into an inflatable catheter balloon that is coupled to the stent. The stent is deployed, for example, by expanding the stent framework with a balloon or by extracting a sheath that allows a self-expandable stent to enlarge after positioning the stent at a desired location within the body. Before clinical use, the stent is sterilized by using conventional medical means.

Figure 2:
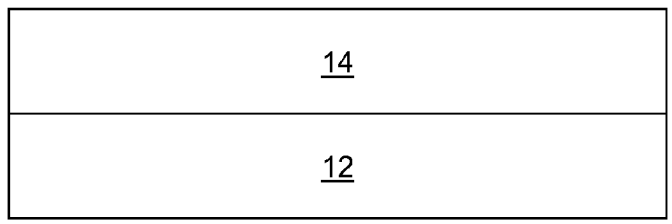
FIG. 2 is a cross-sectional perspective view of a portion of a drug polymer stent for delivering drugs to a vessel in a body, in accordance with one embodiment of the current invention.

FIG. 2 shows a cross-sectional perspective view of a polymer drug stent in accordance with the present invention. Polymer drug stent 10 comprises a stent framework 12 and a drug polymer portion 14.

The stent framework 12 may comprise a metallic base or a polymeric base. In one embodiment, the stent framework comprises a material selected from the group consisting of stainless steel, nitinol, tantalum, MP35N alloy, platinum, titanium, a suitable biocompatible alloy, a suitable biocompatible polymer, or a combination thereof.

Drug polymer portion 14 comprises a polymeric material with at least one therapeutic agent carried thereon. In one embodiment, the polymeric material is a polymer with a semi-hard middle segment with waxy-end segments that will physically aggregate at lower temperatures to form a stable coating but melt easily at elevated temperatures to facilitate removal of the coating. In one embodiment, the polymeric material comprises a waxy remaining portion having enhanced melt properties. In another embodiment, the polymeric material is a material that is relatively insoluble at physiologic conditions but will dissolve rapidly once heated. In one embodiment, the biodegradable polymer is selected from the group consisting of bioproteins, sugar, and dextran.

Figure 3:
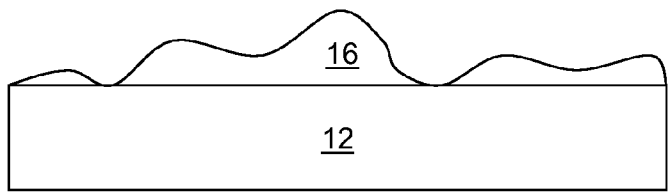
FIG. 3 is a cross sectional perspective view of a portion of a drug-polymer stent framework following drug elution, with a portion of the drug-containing polymer layer remaining thereon.

FIG. 3 shows a cross-sectional perspective view of a stent as in FIG. 2, after the stent 10 is delivered, and the at least one therapeutic agent is eluted, showing the remaining portion 16 of the drug polymer portion 14.

The therapeutic agent may be any suitable therapeutic agent or drug known in the art. In one embodiment, the therapeutic agent is selected from the group consisting of an antisense agent, an antineoplastic agent, an antiproliferative agent, an antithrombogenic agent, an anticoagulant, an antiplatelet agent, an antibiotic, an anti-inflammatory agent, a therapeutic peptide, a gene therapy agent, a therapeutic substance, an organic drug, a pharmaceutical compound, a recombinant DNA product, a recombinant RNA product, an extracellular matrix protein or peptide sequence, such as collagen or collagenic derivatives, a protein, a protein analog, a saccharide, a saccharide derivative, or a combination thereof.

The term "therapeutic agent" includes one or more "therapeutic agents" or "drugs". The terms "therapeutic agents" and "drugs" are used interchangeably and include pharmaceutically active compounds, nucleic acids with and without carrier vectors such as lipids, compacting agents (such as histones), virus (such as adenovirus, adeno-associated virus, retrovirus, lentivirus and a-virus), polymers, antibiotics, hyaluronic acid, gene therapies, proteins, cells, stem cells and the like, or combinations thereof, with or without targeting sequences. Specific examples of therapeutic agents include, for example, pharmaceutically active compounds, proteins, cells, stem cells, oligonucleotides, ribozymes, antisense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA, or siRNA sequences; genomic DNA, cDNA, RNA, or siRNA sequences in a noninfectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, tissue plasminogen activator, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, dephalosporins, aminoglycosides, and nitorfurantoin; anesthetic agents such as lidocaine, buplvacaine, and ropivacaine; nitrix oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability.

In one embodiment, the elution period is from about 24 hours to seven (7) days. In one embodiment, the elution period is about 36 hours. The duration and quantity of therapeutic agent delivered can depend upon the targeted mechanisms of action and the potencies of the therapeutic agents. Typically, elution periods can range from 2 hours to 180 days. In the case of multiple agents (two, three, etc) with one or multiple therapies (i.e., anti-inflammatory and pro-healing agents) the elution kinetics may be such that their dissolution rates may be similar or dissimilar. This dissimilarity can include the timing of the 'burst' (i.e., early in the release or late in the release), relative amount of burst (i.e., percent of total therapeutic agent released over a defined 'short' period), dissolution duration and/or dissolution curve shape (zero order, first order, etc.)

A stent as described herein has many different possible applications. The stent may be used in the cardiovascular system (e.g., in the coronary artery, femoral artery, peripheral arteries or other arteries in the body), the cerebrovascular system, urogenital systems, biliary conduits, abdominal passageways, the gastrointestinal tract or other biological vessels in the body. For example, the stent may be an esophageal stent or biliary stent. Treatment of vascular conditions may include the prevention or correction of various ailments and deficiencies associated with the cardiovascular system, the cerebrovascular system, urogenital systems, biliary conduits, abdominal passageways and other biological vessels within the body. Insertion of the drug polymer stent 10 in a vessel in the body may help treat, for example, heart disease, various cardiovascular ailments, and other vascular conditions. Catheter-deployed drug polymer stent 10 typically is used to treat one or more blockages, occlusions, stenoses, or diseased regions in the coronary artery, femoral artery, peripheral arteries, and other arteries in the body. While the drug polymer portion has been described herein in combination with a stent, it may be applied to other implantable medical devices suitable for drug delivery. For example, the drug polymer portion may be used on guidewires, catheters (including balloon angioplasty catheters), or filters (including vena cava filters). The polymer drug portion may also be applied to other implantable and blood-contacting biomedical devices such as coated pacemaker leads, microdelivery pumps, feeding and delivery catheters, heart valves, artificial livers and other artificial organs.

FIG. 4 is a flow diagram of a method 400 for removing the remaining portion of a drug polymer portion of the stent after delivery of the therapeutic agent is completed. In one embodiment, method 400 is performed using system 100 illustrated in FIGS. 1-3. Method 400 begins at 401. At step 410, a stent 110 is delivered to and implanted at a target region of a vessel. The stent includes a drug polymer coating 14 including an elution portion and a remaining portion 16. As discussed above, the delivered stent may be a balloon expandable stent or a self-expanding stent. Next, the elution portion is eluted from the delivered stent for an elution period (Block 420). The elution period may be from about 24 hours to seven days. In one embodiment, the elution period is 36 hours. In another embodiment, the elution period is between 2 hours and 180 days. After the elution period, the implanted stent is heated (Block 430). Based on the heating of the implanted stent, the remaining portion 16 of the coated stent is removed (Block 440). Method 400 ends at step 450.

FIG. 5 is a flow diagram of a method 500 for delivery of a self-expanding drug delivery stent including an elution portion and a remaining portion. Method 500 begins at 501. Next, a drug polymer coated stent including an elution portion and a remaining portion 16 are provided (Block 510). At step 520, the drug polymer coated stent is deployed on a catheter and covering the stent with a sheath (Block 520), delivering the catheter to a target site in a body lumen, and retracting the sheath to allow the stent to self expand into contact with the lumen (Block 530). The elution portion is eluted from the implanted stent for an elution period (Block 540). After the elution period, the implanted stent is heated (Block 550), and the remaining portion is removed based on the heating (Block 560). In one embodiment, the remaining portion is released from the stent into the vessel without causing thrombogenesis. Method 500 ends at step 570.

FIG. 6 is a flow diagram of a method 600 for delivery of a balloon expandable drug polymer stent. Method 600 begins at 601. The method includes providing a drug polymer stent having a coating with an elution portion and a remaining portion (Block 610), and disposing the coated stent on a catheter over a balloon (Block 620). Method 600 continues by delivering the stent disposed on the catheter to a treatment site in a body lumen, and expanding the balloon to expand the stent into contact with the lumen (Block 630). The elution portion of the implanted stent is eluted for an elution period (Block 640). The implanted stent is heated after the elution period (Block 650), and the remaining portion is removed based on the heating (Block 660). In one embodiment, the remaining portion of the polymeric coating is raised to a temperature above the coating's glass transition temperature. In one embodiment, the polymeric coating is raised to a temperature above the coating's melt flow temperature. In one embodiment, the remaining portion is released from the stent into the vessel without causing thrombogenesis. Method 600 ends at step 670.

Heating the implanted stent as discussed in methods 400, 500 and 600, above, may be accomplished by various methods. FIGS. 7 and 8 illustrate two methods of heating the implanted stent in order to remove the remaining portion of the polymeric coating. FIG. 7 is a flow diagram of one embodiment of a method 700 for heating the implanted stent to remove the remaining portion of the coating. Method 700 begins at 701. Next, the implanted stent is heated after the elution period has elapsed. The implanted stent is heated by delivering magnetic resonance energy to the stent (Block 710). In one embodiment, a MR imaging device is inserted in the body and delivered to the targeted region. Based on heating the implanted stent, the magnetic resonance energy is delivered to the remaining portion of the coating (Block 720). In one embodiment, the remaining portion of the polymeric coating is raised to a temperature above its glass transition temperature (Block 730). In another embodiment, the remaining portion of the polymeric coating is raised to a temperature above the melt flow temperature. In response to being heated to a reflow temperature above its glass transition temperature (or melt flow temperature), the polymeric coating liquefies, is released from the stent and flows in the vessel (Block 740). In one embodiment, the remaining portion is released from the stent into the vessel and into the blood stream without causing thrombogenesis. Method 700 ends at step 750.

FIG. 8 is a flow diagram of an alternative embodiment of a method 800 for heating the implanted stent to remove the remaining portion of the coating. Method 800 begins at 801. Next, the implanted stent is heated by delivering radio frequency energy to the stent (Block 810). Based on the delivery of the radio frequency energy to the stent, radio frequency energy is delivered to the remaining portion of the coating (Block 820). As a result, the remaining portion of the polymeric coating is raised to a temperature above its glass transition temperature or melt flow temperature (Block 830). In response to being heated to a reflow temperature above its glass transition temperature, the remaining portion of the polymeric coating liquefies, is released from the stent and flows into the vessel (Block 840). In one embodiment, the remaining portion of the polymeric coating is released from the stent into the vessel and into the blood stream without causing thrombogenesis. In one embodiment a bare metal stent remains after the remaining portion of the polymeric coating is released. Method 800 ends at step 850.

In one embodiment, the present invention provides a method for treating a vessel in a body. The method includes providing a stent comprising a biodegradable polymeric coating carrying at least one therapeutic agent, the coating being selected from the group consisting of bioproteins, sugar and dextran, the coating having a first delivery configuration and a second, post-delivery configuration comprising a remaining portion of the polymeric coating; delivering the stent to a targeted region of the vessel; allowing the stent to remain in the targeted region in a first configuration for a predetermined length of time for delivery of the at least one therapeutic agent; and removing the remaining portion of the polymeric coating from the stent by heating the stent in situ in the vessel, the polymer coating being substantially removed from the stent based on the heating. In one embodiment, heating the stent includes delivering magnetic resonance energy to the stent. A MR imaging device is inserted in the body and delivered to the targeted region for delivery of the magnetic resonance energy. In an alternative embodiment, the stent is heated by delivering radio frequency energy to the stent. The polymeric coating is raised to a temperature above its glass transition temperature. In response to being heated to a reflow temperature above its glass transition temperature, the polymeric coating liquefies and flows in the vessel. The remaining portion of the polymeric coating is released from the stent into the vessel and into the blood stream without causing thrombogenesis. In one embodiment a bare metal stent remains.

While the invention has been described with reference to particular embodiments, it will be understood by one skilled in the art that variations and modifications may be made in form and detail without departing from the spirit and scope of the invention.

What is claimed is:

1. A method for treating a vascular condition, the method comprising:
   delivering a stent to a target region of a vessel to produce a delivered stent, the stent including a drug polymer coating including a therapeutic agent releasable through action of bodily processes in the vessel;
   maintaining the delivered stent in the vessel for an elution period to elute the therapeutic agent from the delivered stent and produce a reduced stent having a remaining portion of the drug polymer coating; and
   heating the reduced stent after the elution period to remove the remaining portion from the reduced stent.

2. The method of claim 1 wherein the therapeutic agent is carried in an elution portion comprising a biodegradable polymer carrying at least one therapeutic agent.

3. The method of claim 2 wherein the biodegradable polymer is selected from the group consisting of bioproteins, sugar, and dextran.

4. The method of claim 3 wherein the at least one therapeutic agent is selected from the group consisting of an antisense agent, an antineoplastic agent, an antiproliferative agent, an antithrombogenic agent, an anticoagulant, an antiplatelet agent, an antibiotic, an anti-inflammatory agent, a therapeutic peptide, a gene therapy agent, a therapeutic substance, an organic drug, a pharmaceutical compound, a recombinant DNA product, a recombinant RNA product, an extracellular matrix protein or peptide sequence, such as collagen or collagenic derivatives, a protein, a protein analog, a saccharide, a saccharide derivative, or a combination thereof.

5. The method of claim 1 wherein the elution period is between 2 hours and 180 days.

6. The method of claim 1 wherein heating the reduced stent comprises delivering magnetic resonance energy to the reduced stent.

7. The method of claim 6 wherein a MR imaging device is inserted in the body and delivered to the targeted region for delivery of the magnetic resonance energy.

8. The method of claim 1 wherein the reduced stent is heated by delivering radio frequency energy to the reduced stent.

9. The method of claim 1 wherein the remaining portion of the polymeric coating is raised to a temperature above its melt flow temperature.

10. The method of claim 1 wherein the remaining portion is released from the reduced stent into the vessel.

11. A method for treating a vessel in a body, the method comprising:
    providing a stent comprising a biodegradable polymeric coating carrying at least one therapeutic agent releasable through action of bodily processes in the vessel, the coating being selected from the group consisting of bioproteins, sugar and dextran, the coating having a first delivery configuration and a second, post-delivery configuration comprising a remaining portion of the coating;
    delivering the stent with the coating in the first delivery configuration to a targeted region of the vessel;
    allowing the stent to remain in the targeted region for a predetermined length of time for elution of the at least one therapeutic agent and conversion of the coating from the first delivery configuration to the second, post-delivery configuration;
    removing the remaining portion of the coating from the stent by heating the stent in situ in the vessel, the coating being substantially removed from the stent based on the heating.

12. The method of claim 11 wherein heating the stent comprises delivering magnetic resonance energy to the stent.

13. The method of claim 12 wherein a MR imaging device is inserted in the body and delivered to the targeted region for delivery of the magnetic resonance energy.

14. The method of claim 11 wherein the stent is heated by delivering radio frequency energy to the stent.

15. The method of claim 11 wherein the polymeric coating is raised to a temperature above its glass transition temperature.

16. The method of claim 11 wherein the remaining portion of the polymeric coating is released from the stent into the vessel.

17. A method for treating a vessel in a body, the method comprising the steps of:
    providing a polymer coated drug delivery stent including a polymer coating carrying at least one therapeutic agent releasable through action of bodily processes in the vessel;
    delivering the stent to a targeted region of the vessel;
    allowing the delivered stent to remain in the targeted region for a predetermined period of time during which the polymeric coating elutes the at least one therapeutic agent to the targeted region of the vessel and becomes a remaining portion of the polymer coating on the delivered stent;

after elution of the therapeutic agent, heating the stent and releasing the remaining portion of the polymer coating into the vessel while leaving the stent in the targeted region of the vessel, and substantially removing the remaining portion of the polymer coating from the stent based on the heating.

18. The method of claim 17, wherein the remaining portion of the polymer coating is locally heated to a reflow temperature above its glass transition temperature, so that the excess polymeric coating liquefies and flows into the vessel.

19. The method of claim 17, wherein the stent is metal, and the step of substantially removing the remaining portion of the polymer coating comprises leaving a bare metal stent.

20. The method of claim 17 wherein the stent is heated by delivering radio frequency energy or magnetic resonance energy to the stent.

\* \* \* \* \*